United States Patent
Starner et al.

(10) Patent No.: US 6,441,238 B1
(45) Date of Patent: Aug. 27, 2002

(54) N-(AMINOPROPYL)-TOLUENEDIAMINES AND THEIR USE AS EPOXY CURING AGENTS

(75) Inventors: William Edward Starner, Nesquehoning; Tammy Lynn Cush, Whitehall, both of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/024,974

(22) Filed: Dec. 19, 2001

(51) Int. Cl.$^7$ ............................................. C07C 211/00
(52) U.S. Cl. ....................... 564/367; 528/422
(58) Field of Search ........................... 564/367; 528/422

(56) References Cited

FOREIGN PATENT DOCUMENTS

EP   0067593    12/1982
JP   2963739    10/1999

OTHER PUBLICATIONS

"Handbook of Epoxy Resins" by H. Lee and K. Neville, McGraw Hill Book Co. 1967.
Ashcroft, W.R., "Curing Agents for Epoxy Resins," in B. Ellis (ed.).
"Chemistry and Technology of Epoxy Resins," Blackie Academic and Professional, London (1993).
Eldefield, et al., 68 J. Amer. Chem. Soc. 1262 (1949).
Cookson, et al., "The Cyanoethylation of Amines and Arsines," J. Chem. Soc. 1949.
Braunholtz, et al., "The Preparation of Bis(2–cyanoethyl) Derivatives of Aromatic Primary Amines, and Their Conversation into 1:6–Diketojulolidines," J. Chem. Soc., 1952.
Braunholtz, et al., "The Preparation of Bis(2–cyanoethyl) Derivatives of Aromatic Primary Amines, and Their Conversion into 1:6–Diketojulolidines, Part II," J. Chem. Soc., 1953.

*Primary Examiner*—Samuel Barts
(74) *Attorney, Agent, or Firm*—Michael Leach

(57) ABSTRACT

The invention provides N-aminopropylated toluenediamines, processes for synthesizing them, compositions containing them and methods for using them to cure epoxy resins. In preferred embodiments, the N-aminopropylated toluenediamines are represented by the following formula:

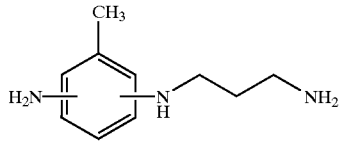

where the nitrogen atoms are ortho or meta to each other on the aromatic ring.

31 Claims, No Drawings

N-(AMINOPROPYL)-TOLUENEDIAMINES AND THEIR USE AS EPOXY CURING AGENTS

BACKGROUND OF THE INVENTION

This invention relates to aminopropylated aromatic amines, more particularly to N-(aminopropyl)-ortho-toluenediamine, N-(aminopropyl)-meta-toluenediamine and their use as epoxy curing agents.

It is known to use amines, such as aliphatic or aromatic amines, for the curing of epoxy resins. See, e.g., "Handbook of Epoxy Resins" by H. Lee and K. Neville, McGraw Hill Book Co., 1967. The epoxy industry, particularly the adhesive, composite and syntactic foam markets of the industry, is in need of a low viscosity aromatic amine curing agent fairly rapid in reactivity and heat generation while providing high Tg, good fracture toughness and chemical resistance after full cure. Additionally, the civil engineering epoxy market has particular interest in finding new amine curatives that combine the rapid curing rate of aliphatic amines with the good chemical resistance typically found in aromatic amine curatives, such as MDA and DETDA.

Low viscosity amine curing agents are typically aliphatic amines, cycloaliphatic amines or amidoamines. These amine curatives provide the appropriate viscosity and in some cases adequate fracture toughness for adhesive, composite and syntactic foam applications, but are not suitable for many applications in that they are too reactive and do not provide high Tg and good chemical resistance. For civil engineering applications, these amine curatives sometimes have the appropriate reactivity and viscosity, but do not provide adequate chemical resistance. Aromatic amines, on the other hand, provide high Tg, good fracture toughness and excellent chemical resistance for adhesive, composite and syntactic foam applications but are less than ideal in that they are usually high viscosity liquids or solids, have extremely long potlifes and high toxicity. For civil engineering applications aromatic amine curatives provide good chemical resistance but are slow in reactivity and present toxicity issues as well.

The epoxy industry has employed many types of curative blends in an attempt to maximize the desired application properties, but in most cases at the expense of other properties. Additives such as accelerators, tougheners, reactive diluents and non-reactive diluents are employed to maximize a desired property but again to the deterioration of other properties. A number of good references are available on this subject including: Lee and Neville's, "Handbook of Epoxy Resins," cited above, and W. R. Ashcroft, "Curing Agents for Epoxy Resins," in B. Ellis (ed.). "Chemistry and Technology of Epoxy Resins," Blackie Academic and Professional, London (1993), pp. 37–73.

Others in the epoxy industry have developed novel amines in attempting to optimize curative properties. For example, Japanese Patent 2963739 (1999) describes the use of substituted-N-phenyl-1,3-propanediamines as liquid epoxy curatives which do not B-stage during cure and thus yield a fully cured epoxy resin. The substituted-N-phenyl-1,3-propanediamines described therein are represented by the following chemical formula:

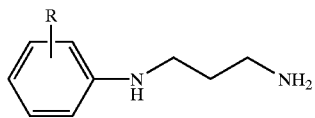

where R is hydrogen, lower alkyl group, lower alkoxyl group or halogen. Although the method of synthesis of these curatives is not disclosed, other references teach methods for synthesizing aromatic amines.

For example, European Patent 0 067 593 (1982) describes the cyanoethylation of para, meta, and ortho phenylenediamine to generate 3,3'-(p,m or o-phenylenedi-imino)-dipropanenitrile:

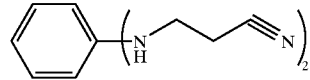

EP 0 067 593 teaches the use of water as the solvent and concentrated hydrochloric acid as the catalyst to obtain the dicyanoethylated product.

Elderfield et al., 68 J. Amer. Chem. Soc. 1262 (1949), describes the synthesis of β-p-anisidinopropionitrile by boiling p-anisidine and acrylonitrile in acetic acid.

Cookson et al., "The Cyanoethylation of Amines and Arsines," J. Chem. Soc. 1949, pp. 67–72, describes the cyanoethylation of aniline by heating to 150° C. a mixture of aniline and acrylonitrile in the presence of excess acetic acid in an autoclave to generate 2-cyanoethylaniline and bis-2-cyanoethylaniline. The reference further describes the reaction of diphenylamine and acrylonitrile in an excess of acetic acid using a catalytic amount of fine copper powder to generate diphenyl-2-cyanoethylamine.

Braunholtz et al., "The Preparation of Bis(2-cyanoethyl) Derivatives of Aromatic Primary Amines, and Their Conversion into 1:6-Diketojulolidines," J. Chem. Soc., 1952, pp. 3046–3051, describes the cyanoethylation of aniline, m-toluidine, p-toluidine, p-anisidine and p-chloroaniline in an excess of acetic acid.

Braunholtz et al., "The Preparation of Bis(2-cyanoethyl) Derivatives of Aromatic Primary Amines, and Their Conversion into 1:6-Diketojulolidines. Part II," J. Chem. Soc., 1953, pp. 1817–1824, describes the cyanoethylation of several different aromatic primary monoamines in an excess of acetic acid using various metal catalysts to selectively generate mono and di-cyanoethylated derivatives.

All references cited herein are incorporated herein by reference in their entireties.

BRIEF SUMMARY OF THE INVENTION

The invention provides aminopropylated toluenediamines, processes for synthesizing them, compositions containing them and methods for using them to cure epoxy resins. In preferred embodiments, the aminopropylated toluenediamines are represented by the following formula:

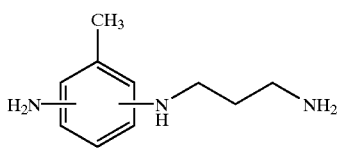

where the nitrogen atoms are ortho or meta to each other on the aromatic ring.

With regard to the present invention and throughout the specification and claims the terms "aminopropyl toluenediamine(s)", "aminopropylated toluenediamine(s)", "N-(aminopropyl) toluenediamine(s)" and "N-(aminopropylated) toluenediamine(s)" are used interchangeably.

DETAILED DESCRIPTION OF THE INVENTION

The most preferred aminopropylated toluenediamines of the invention are suitable for use as epoxy resin curing agents. Aminopropylated toluenediamines where the nitrogen atoms are ortho or meta to each other on the aromatic ring have been found to be particularly suitable for this purpose. Thus, the most preferred aminopropylated toluenediamines of the invention are aminopropylated products of ortho-toluenediamine represented by the following Formulas I–IV:

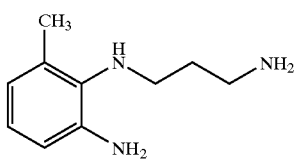

N-(2-amino-6-methylphenyl)-
1,3-propanediamine (I)

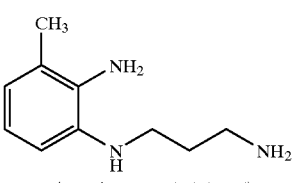

N-(2-amino-3-methylphenyl)-
1,3-propanediamine (II)

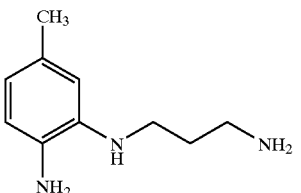

N-(2-amino-5-methylphenyl)-
1,3-propanediamine (III)

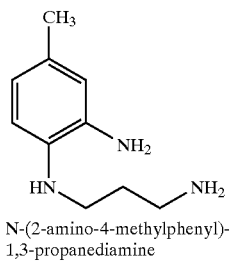

N-(2-amino-4-methylphenyl)-
1,3-propanediamine (IV)

and aminopropylated products of meta-toluenediamine represented by the following Formulas V–VII:

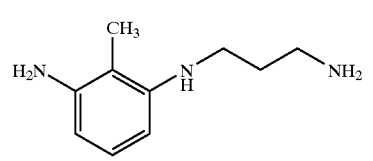

N-(5-amino-6-methylphenyl)-
1,3-propanediamine (V)

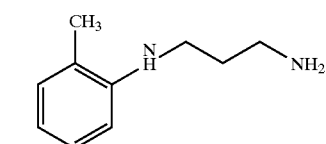

N-(3-amino-6-methylphenyl)-
1,3-propanediamine (VI)

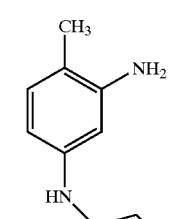

N-(3-amino-4-methylphenyl)-
1,3-propanediamine (VII)

Formulas I–IV above are the aminopropylated products of ortho-toluenediamine (OTD). Formulas I–II are based on 2,3-toluenediamine (TDA) and the Formulas III–IV are based on 3,4-TDA. A commercial isomer mix of OTD is typically 60/40 2,3-TDA/3,4-TDA. Using commercial grade OTD therefore leads to aminopropylated isomer mixtures.

Formulas V–VII above are the aminopropylated products of meta-toluenediamine (MTD). Formula V is based on 2,6-TDA and Formulas VI and VII are based on 2,4-TDA.

Preparation of Aminopropylated TDA

Aminopropylated products of OTD are prepared by two reaction steps. As shown in Equations I and II (below), OTD is initially cyanoethylated by reaction with acrylonitrile (ACN) at elevated temperature in the presence of an acid and a protic solvent (e.g., water) for a period of time adequate for reaching the desired extent of conversion to the cyanoethylated product. The resulting cyanoethylated TDA is then hydrogenated under pressure (e.g., 900 psi or 6.21 Mpa) and temperature using a hydrogenation catalyst (e.g., Raney cobalt or nickel). The resulting aminopropylated TDA is then purified by reduced pressure fractional distillation.
Cyanoethylation of Orthotoluenediamine (Eq. I)

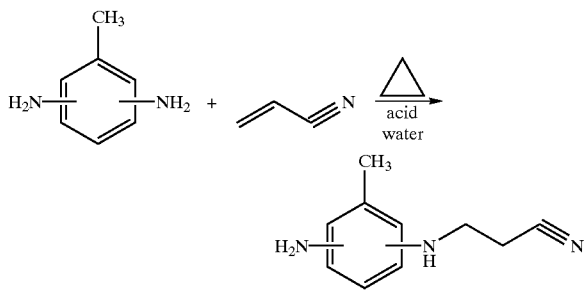

Hydrogenation of Cyanoethylated Orthotoluenediamine (Eq. II)

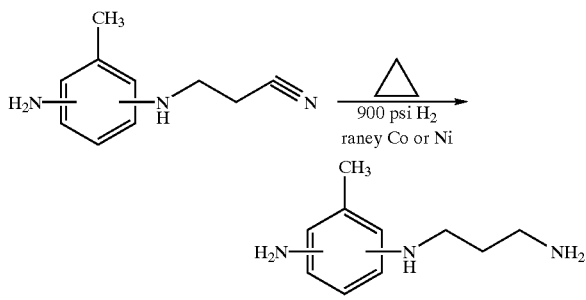

Aminopropylated products of MTD are prepared by two reaction steps. As shown in Equations III and IV, MTD is initially cyanoethylated by reaction with ACN at elevated temperature in the presence of an acid and a protic solvent (e.g., water) for a period of time adequate for reaching the desired extent of conversion to the cyanoethylated product. The resulting cyanoethylated TDA is then hydrogenated under pressure (e.g., 900 psi or 6.21 Mpa) and temperature using a hydrogenation catalyst (e.g., Raney cobalt or nickel). The resulting aminopropylated TDA is then purified by reduced pressure fractional distillation.
Cyanoethylation of Metatoluenediamine (Eq. III)

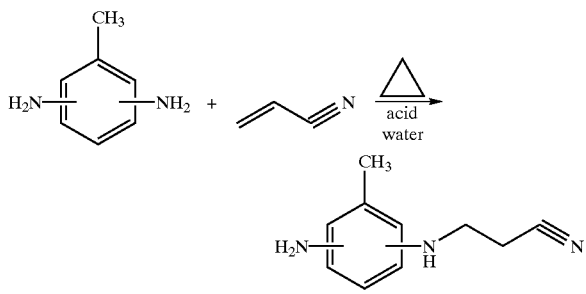

Hydrogenation of Cyanoethylated Metatoluenediamine (Eq. IV)

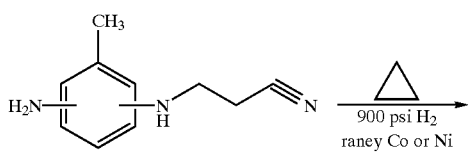

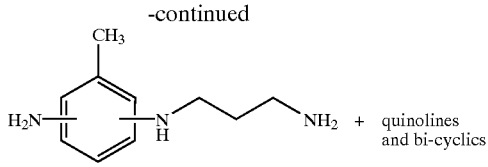 + quinolines and bi-cyclics

In the preparation of aminopropylated OTD, either the pure compounds 2,3-TDA or 3,4-TDA, or isomer mixtures, such as 60/40 2,3-TDA/3,4-TDA, can be reacted with ACN. In fact, any blend or mixture of the TDA isomers may be used. The preferred reactant mixture comprises commercial grade OTD.

In the preparation of aminopropylated MTD, either the pure compounds 2,4-TDA, 2,6-TDA, or isomer mixtures such as 80/20 2,4-TDA/2,6-TGA can be reacted with ACN. Any blend or mixture of the TDA isomers can be used. The preferred reactant mixture comprises commercial grade MTD.

The molar ratio of reactants, moles of OTD and/or MTD to moles of ACN, can vary from about 10:1 to about 1:10. The molar ratio used will affect the rate of reaction and the product distribution, but as the final product is distilled the final product quality is unaffected. To maximize yield and efficiency, the desired molar ratio is from 0.95:1.0 to about 1.0:2.0 with the optimum being about 1.0:1.2.

The cyanoethylation reaction is conducted using at least one acid catalyst. The acid catalyst can be any mineral, carboxylic, super or supported acid, including but not limited to hydrochloric acid, sulfuric acid, phosphoric acid, acetic acid, propionic acid, para-toluenesulfonic acid, triflic acid (trifluoromethanesulfonic acid) and Nafion® super acid catalyst from DuPont, which is a bead-form, strongly acidic resin, i.e., a copolymer of tetrafluoroethylene and perfluoro-3,6-dioxa-4-methyl-7-octenesulfonyl fluoride, converted to the proton (H+) form. The preferred acid catalysts are hydrochloric acid and Nafion catalyst with Nafion catalyst being most preferred.

Any protic solvent can be used in the cyanoethylation, including but not limited to water, methanol, ethanol, isopropanol, n-propanol, etc.

The cyanoethylation reaction can be conducted over a temperature range from about 50° C. to about 150° C. within a pressure range from about atmospheric pressure up to about 900 psi (6.21 MPa). The reaction time is dependent on the reaction temperature, pressure and the desired extent of the reaction as measured by gas chromatography (GC). The reaction of TDA with ACN can generate not only a mono-cyanoethylated product (CNTDA) but also a di-cyanoethylated product (DCNTDA). Thus, at any given time during the cyanoethylation there is, for example, a mixture of unreacted TDA, CNTDA and DCNTDA, as described according to the following Equation V:

(Eq. V)

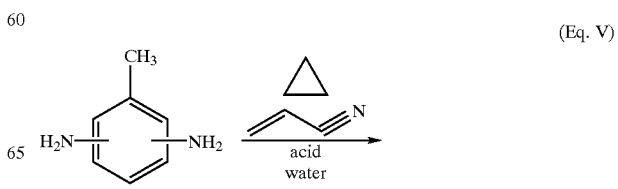

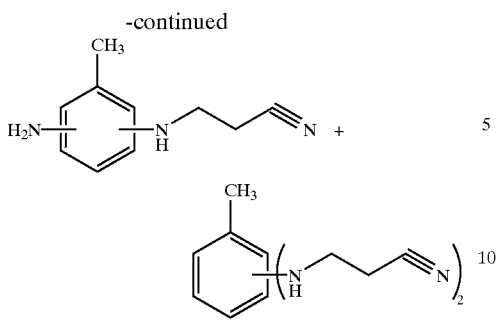

The cyanoethylation reaction and products produced thereby are disclosed and claimed in the inventors' copending U.S. patent application, having the Attorney Docket No. 06231USA, entitled "CYANOETHYLATED ORTHO AND METATOLUENEDIAMINE COMPOSITIONS AND PROCESS FOR MAKING THEM", and filed on even date with the present application.

Hydrogenation Step

The cyanoethylated product mixture is converted to crude aminopropylated TDA (APTDA) by catalytic hydrogenation. The product mixture from the cyanoethylation step is carried through to the aminopropylated form, i.e., the unreacted TDA remains in the aminopropylated product mix unaffected, and the CNTDA and DCNTDA are both hydrogenated to the aminopropylated forms APTDA and diaminopropylated TDA (DAPTDA).

When the cyanoethylated product mixture comprises cyanoethylated MTD, hydrogenation not only produces mono- and di-aminopropylated MTD, but also produces the quinolines and di-cyclized byproducts shown below:

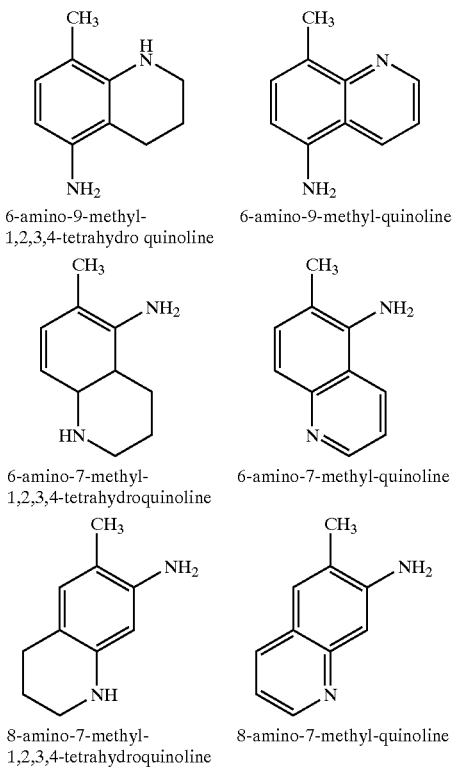

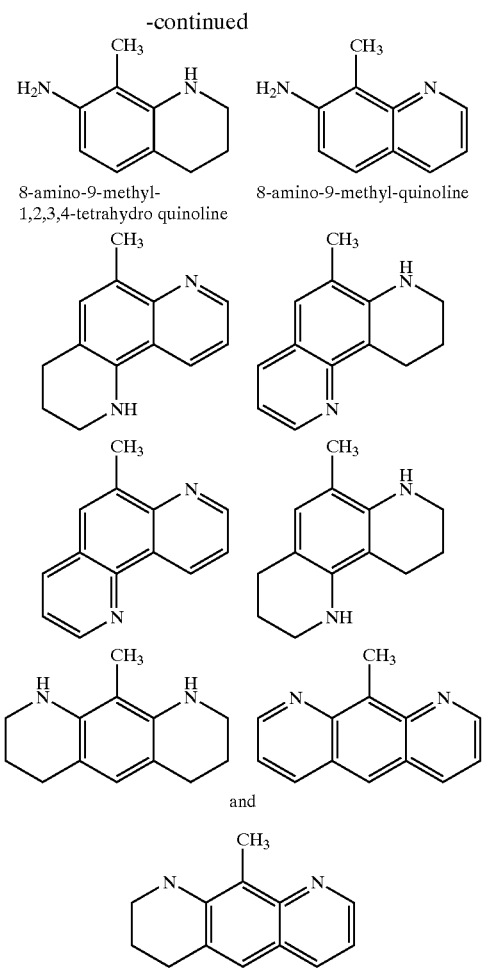

The final composition may contain cyclics ranging from 5 to 50% depending on the fractional distillation conditions employed to purify the product. For example, a typical product mixture comprises about 9% TDA, 16% quinolines, 50% aminopropyl-m-TDA and 16% dicyclic products.

The hydrogenation can be conducted using the product obtained directly from the cyanoethylation or the solvent may be removed. Any solvent known to one skilled in the art can also be used.

The hydrogenation can be conducted over a temperature range from room temperature up to about 200° C. Higher temperatures may lead to reforming of the amine mixture and should be avoided. A preferred temperature range is from 50–125° C., which permits an adequate temperature differential for good heat removal. The most preferred temperature range is about 100–125° C.

The hydrogenation can be conducted at a hydrogen pressure ranging from atmospheric pressure to about 2000 psi (13.79 MPa). Higher or lower pressures may be used without causing a detrimental affect to the product. The ideal hydrogen pressure range is from about 50 to 900 psi (0.34 to 6.21 MPa) with the optimum being 500 to 900 psi (3.45 to 6.21 MPa).

Any hydrogenation catalyst known to be active toward nitrile hydrogenation can be used. Preferred catalysts include Raney nickel and Raney cobalt, with Raney cobalt being most preferred.

The catalyst loading is preferably from 0.01 to 10.0% by weight of the reactant charge, with about 0.5 to about 2.0% being most preferred.

Purification

The crude product resulting from the steps above is a mixture of starting TDA, the desired mono-aminopropylated TDA, di-aminopropylated TDA, and where MTD is a reactant, quinolines and di-cyclized byproducts. The composition of the crude product will vary depending on the reaction conditions, catalyst type and reaction time. Typical composition ranges for OTD-based reactions are 20/70/10 to 5/75/20 weight % OTD/mono-APTDA/di-APTDA. Typical composition ranges for MTD-based reactions are 20/15/50/15 to 5/25/45/25 weight % TDA/quinolines/APTDA/dicyclics. Although the crude products are satisfactory as curatives for epoxy resins, it is more desirable to use the purified APTDA. This purification may be accomplished by any method known to one skilled in the art, but the preferable method is reduced pressure fractional distillation, again a method well known to the art. Depending on the distillation conditions and separation capability of the distillation, the purified product from an OTD-based reaction can have an assay ranging from about 90 to 99.9%, with the chief impurities being OTD and di-APTDA (neither of which will impair the performance attributes imparted by this curative to a cured epoxy resin formulation). Depending on the distillation conditions and separation capability of the distillation, the purified product from a MTD-based reaction may have a composition ranging from 1/15/64/15 to 0/12/76/12 TDA/quinolines/APTDA/dicyclics, respectively. However, the compositional possibilities are endless. Again, none of the possible compositions will impair the performance attributes imparted by this curative to a cured epoxy resin formulation.

Use of New Aminopropylated Aromatic Amines in Epoxy Formulations

In addition to being low viscosity, the aminopropylated aromatic amines of the invention provide excellent curatives for ambient and heat-cured epoxy formulations. In ambient-cured epoxies, APTDA provides short gel and thin film set times, not typical of aromatic amines, while providing excellent physical property development such as hardness, gloss and chemical resistance as typically seen with aromatic amine curatives. In heat-cured epoxy formulations, APTDA provides unexpectedly high glass transition temperature (Tg).

The crude, purified and high purity grades of APTDA are mixed thoroughly with an epoxy resin and optionally heated to effect curing. The stoichiometry employed preferably ranges from 0.5 N-H equivalent of the APTDA per equivalent of epoxide moieties in the epoxy resin to 1.5 N-H equivalent of the APTDA per equivalent of epoxide. More preferably, the stoichiometry ranges from 0.9 to 1.1 N-H equivalent per epoxide with a 1.0:1.0 ratio being most preferred.

Any epoxy resin can be employed, including but not limited to the diglycidyl ether of bisphenol A and/or bisphenol F. Solvents such as an alcohol, phenol, aliphatic or aromatic hydrocarbon, esters, ethers and the like can be used. Reactive diluents such as aromatic and aliphatic glycidyl ethers and esters can also be used as well as various types of fillers and colorants.

The invention will be illustrated in more detail with reference to the following Examples, but it should be understood that the present invention is not deemed to be limited thereto.

EXAMPLE 1

Cyanoethylation of 3,4-Toluenediamine using Nafion Catalyst

A 3000 ml 4-necked round bottom flask was equipped with a mechanical stirrer, thermometer, condenser, nitrogen purge and dropping funnel. The vessel was charged with 500 parts of 3,4-toluenediamine, 436 parts of deionized water and 3.0 parts of Nafion catalyst. The mixture was heated to 80–86° C. and 322 parts of ACN were added drop-wise over a thirty-minute period. The mixture was refluxed for 11 hours, cooled to room temperature and collected. The organic phase of the reaction mixture contained 3.2% acrylonitrile, 5.4% 3,4-toluenediamine, 80.1% mono-cyanoethylated 3,4-toluenediamine (CN-3,4-OTD) and 11.2% di-cyanoethylated 3,4-toluenediamine (DCN-3,4-OTD), according to gas chromatographic (GC) analysis.

Hydrogenation of Cyanoethylated 3,4-Toluenediamine

This cyanoethylated product mixture was then placed in an autoclave, treated with 250 ml of 25% ammonium hydroxide to neutralize the acid catalyst and destroy the unreacted ACN. 25 g of Raney cobalt catalyst were then added. The autoclave was sealed, purged 2 times with nitrogen and 2 times with hydrogen, and then pressurized to 900 PSI (6.21 MPa) with hydrogen. The temperature was raised to 125° C. under constant 900 PSI (6.21 MPa) hydrogen pressure. The temperature was held at 125° C. until the hydrogen consumption ceased which usually takes about 30 minutes. The autoclave was cooled to room temperature, hydrogen vented and purged with nitrogen. The crude AP-3,4-OTD was then filtered to remove the catalyst. The resultant product mixture as analyzed by GC contained 20.3% 3,4-OTD, 71.5% AP-3,4-OTD and 7.1% DAP-3,4-OTD.

Purification of Crude Aminopropylated 3,4-Toluenediamine

The crude AP-3,4-OTD was purified by reduced pressure fractional distillation using a 48-inch packed column and refluxed splitter. The distillation conditions were 20 mm Hg and 2:1 reflux ratio. The heart cut was taken over a temperature range of 160–168° C. 522 g of clear, colorless 98%+ AP-3,4-OTD were obtained. The viscosity was 285 cps @ 25° C. and the amine value was 624 meq KOH/g.

Use of Purified Aminopropylated 3,4-Toluenediamine as Epoxy Curative

The pure AP-3,4-OTD was mixed with Epon 828 epoxy resin and evaluated for gel time and thin film set time. Standard methods ERF 13-70, ERF 2-82 and ASTM D 2471-94 were used to measure gel time and standard methods ASTM D 5895-96 was used to measure thin film set time. Both the Epon 828 epoxy resin and the AP-3,4-OTD were placed in a incubator over night at 25° C. 23.89 g of AP-3,4-OTD was added to 126.1 g of Epon 828 epoxy resin and mixed thoroughly for 1 minute prior to measuring the gel time and thin film set time. The resulting gel time and thin film set time were 110.9 minutes and 5.0 hours, respectively. The Differential Scanning Calorimeter (DSC) data was: Onset Temperature of 66° C.; Maximum Heat of 113° C.; ΔH of 433 j/g and Tg of 155.4° C.

EXAMPLE 2

Cyanoethylation of 60/40 2,3-/3,4-OTD Using Hydrochloric Acid as Catalyst

A 2000 ml 4-necked round bottom flask was equipped with a magnetic stir bar and stirrer, thermometer, condenser, nitrogen purge and dropping funnel. The vessel was charged with 523 parts of OTD, 502 parts of deionized water and 0.3 parts of concentrated hydrochloric acid. The mixture was heated to 80–86° C. and 477 parts of ACN were added drop-wise over a 30-minute period. The mixture was refluxed for 28 hours, cooled to room temperature and collected. The organic phase of the reaction mixture contained 15.4% ACN, 10.4% OTD, 59.8% mono-cyanoethylated 2,3-/3,4-toluenediamine (CNOTD) and 13.6% di-cyanoethylated 2,3-/3,4-toluenediamine (DCNOTD), according to GC analysis.

EXAMPLE 3

Cyanoethylation of OTD Using Nafion Catalyst

A 2000 ml 4-necked round bottom flask was equipped with a magnetic stir bar and stirrer, thermometer, condenser, nitrogen purge and dropping funnel. The vessel was charged with 523.5 parts of OTD, 505 parts of deionized water and 1.0 parts of Nafion catalyst. The mixture was heated to 80–86° C. and 477 parts of ACN were added drop-wise over a 30-minute period. The mixture was refluxed for 23 hours, cooled to room temperature and collected. The organic phase of the reaction mixture contained 8.8% ACN, 19.5% OTD, 61.1% CNOTD and 9.8% DCNOTD according to GC analysis.

EXAMPLE 4

Hydrogenation of Cyanoethylated OTD

The crude CNOTD obtained in Examples 2 and 3 were combined, placed in an autoclave and treated with 500 ml of 28% ammonium hydroxide. 50 g of Raney cobalt catalyst were then added. The autoclave was sealed, purged 2 times with nitrogen and 2 times with hydrogen, and then pressurized to 900 PSI (6.21 MPa) with hydrogen. The temperature was raised to 125° C. under constant 900 PSI (6.21 MPa) hydrogen pressure. The temperature was held at 125° C. until the hydrogen consumption ceased, which usually takes about 30 minutes. The autoclave was cooled to room temperature, hydrogen vented and purged with nitrogen. The crude APOTD was then filtered to remove the catalyst. The resultant product mixture as analyzed by GC contained 22.8% OTD, 61.6% APOTD and 10.1% DAPOTD.

Purification of Crude APOTD

The crude APOTD was purified by reduced pressure fractional distillation using a 48-inch packed column and refluxed splitter. The distillation conditions were 20 mm Hg and 2:1 reflux ratio. The heart cut was taken over a temperature range of 161–168° C. 1075 g of clear, colorless 98%+APOTD were obtained. The viscosity was 514 cps @ 25° C.

Use of purified APOTD as Epoxy Curative

The pure APOTD was mixed with Epon 828 epoxy resin and evaluated for gel time and thin film set time. Standard methods ERF 13-70, ERF 2-82 and ASTM D 2471-94 were used to measure gel time and standard methods ASTM D 5895-96 was used to measure thin film set time. Both the Epon 828 epoxy resin and the APOTD were placed in a incubator over night at 25° C. 23.88 g of APOTD were added to 126.1 g of Epon 828 epoxy resin and mixed thoroughly for 1 minute prior to measuring the gel time and thin film set time. The resulting gel time and thin film set time were 122.9 minutes and 5.5 hours, respectively. The Tg by DSC was 152° C.

EXAMPLE 5

Cyanoethylation of 3,4-Toluenediamine Using 1-Propanol as Solvent

A 500 ml 4-necked round bottom flask was equipped with a magnetic stir bar and stirrer, thermometer, condenser, nitrogen purge and dropping funnel. The vessel was charged with 104.8 parts of 3,4-toluenediamine, 100 parts of 1-propanol and 0.3 parts of Nafion catalyst. The mixture was heated to 80–86° C. and 95 parts of acrylonitrile were added drop-wise over a 30-minute period. The mixture was refluxed for 46 hours, cooled to room temperature and collected. The organic phase of the reaction mixture contained 10.3% acrylonitrile, 25.6% 3,4-toluenediamine, 50.9% mono-cyanoethylated 3,4-toluenediamine and 7.2% di-cyanoethylated 3,4-toluenediamine according to GC analysis.

EXAMPLE 6

Cyanoethylation of 2,4-Toluenediamine Using Hydrochloric Acid as Catalyst

A 250 ml 4-necked round bottom flask was equipped with a magnetic stir bar and stirrer, thermometer, condenser, nitrogen purge and dropping funnel. The vessel was charged with 54 parts of 2,4-toluenediamine, 50 parts of deionized water and 0.3 parts of concentrated hydrochloric acid. The mixture was heated to 80–86° C. and 48 parts of acrylonitrile were added drop wise over a 30-minute period. The mixture was refluxed for 37 hours, cooled to room temperature and collected. The organic phase of the reaction mixture contained 7.9% acrylonitrile, 0.4% 2,4-toluenediamine, 66.8% mono-cyanoethylated 2,4-toluenediamine and 21.1% di-cyanoethylated 2,4-toluenediamine, according to GC analysis.

EXAMPLE 7

Cyanoethylation of 2,4-Toluenediamine Using Nafion Catalyst

A 3000 ml 4-necked round bottom flask was equipped with a mechanical stirrer, thermometer, condenser, nitrogen purge and dropping funnel. The vessel was charged with 722 parts of 2,4-toluenediamine, 630 parts of deionized water and 3.2 parts of Nafion catalyst. The mixture was heated to 80–86° C. and 465 parts of acrylonitrile were added drop-wise over a 30-minute period. The mixture was refluxed for 7 hours, cooled to room temperature and collected. The organic phase of the reaction mixture contained 4.6% acrylonitrile, 8.1% 2,4-toluenediamine, 76.3% mono-cyanoethylated 2,4-toluenediamine and 9.8% di-cyanoethylated 2,4-toluenediamine according to GC analysis.

EXAMPLE 8

Cyanoethylation of 2,6-Toluenediamine Using Hydrochloric Acid as Catalyst

A 250 ml 4-necked round bottom flask was equipped with a magnetic stir bar and stirrer, thermometer, condenser, nitrogen purge and dropping funnel. The vessel was charged with 49 parts of 2,6-toluenediamine, 50 parts of deionized water and 0.3 parts of concentrated hydrochloric acid. The mixture was heated to 80–86° C. and 47.5 parts of acrylonitrile were added drop-wise over a 30-minute period. The mixture was refluxed for 40 hours, cooled to room temperature and collected. The organic phase of the reaction mixture contained 13.3% acrylonitrile, 5.0% 2,6-toluenediamine, 54.4% mono-cyanoethylated 2,6-toluenediamine and 24.1% di-cyanoethylated 2,6-toluenediamine according to GC analysis.

EXAMPLE 9

Cyanoethylation of 2,6-Toluenediamine Using Nafion Catalyst

A 3000 ml 4-necked round bottom flask was equipped with a mechanical stirrer, thermometer, condenser, nitrogen purge and dropping funnel. The vessel was charged with 570 parts of 2,6-toluenediamine, 497 parts of deionized water and 3.0 parts of Nafion catalyst. The mixture was heated to 80–86° C. and 367 parts of acrylonitrile were added drop-wise over a 30-minute period. The mixture was refluxed for 15 hours, cooled to room temperature and collected. The organic phase of the reaction mixture contained 6.9% acrylonitrile, 17.1% 2,6-toluenediamine, 60.4% mono-cyanoethylated 2,6-toluene-diamine and 15.4% di-cyanoethylated 2,6-toluenediamine according to GC analysis.

EXAMPLE 10

Cyanoethylation of 80/20 2,4-/2,6-Toluenediamine Using Nafion Catalyst

A 250 ml 4-necked round bottom flask was equipped with a magnetic stir bar and stirrer, thermometer, condenser, nitrogen purge and dropping funnel. The vessel was charged with 55.1 parts of 80/20 2,4-/2,6-toluenediamine, 55 parts of deionized water and 0.3 parts of Nafion catalyst. The mixture was heated to 80–86° C. and 48 parts of acrylonitrile were added drop-wise over a 30-minute period. The mixture was refluxed for 24 hours, cooled to room temperature and collected. The organic phase of the reaction mixture contained 9.2% acrylonitrile, 2.9% 2,4-/2,6-toluenediamine, 65.8% mono-cyanoethylated 2,4-/2,6-toluenediamine and 22.1% di-cyanoethylated 2,4-/2,6-toluenediamine according to GC analysis.

EXAMPLE 11

Hydrogenation of Cyanoethylated 2,4-Toluenediamine

The crude cyanoethylated 2,4-toluenediamine obtained in Examples 6 and 7 were combined, placed in an autoclave and treated with 500 ml of 28% ammonium hydroxide. 50 g of Raney cobalt catalyst were then added. The autoclave was sealed, purged 2 times with nitrogen and 2 times with hydrogen, and then pressurized to 900 PSI (6.21 MPa) with hydrogen. The temperature was raised to 125° C. under constant 900 PSI (6.21 MPa) hydrogen pressure. The temperature was held at 125° C. until the hydrogen consumption ceased, which usually takes about 30 minutes. The autoclave was cooled to room temperature, hydrogen vented and purged with nitrogen. The crude aminopropylated 2,4-toluenediamine was then filtered to remove the catalyst. The resultant product mixture as analyzed by GC contained 12.7% propylamine, 7.7% 2,4-TDA, 14.3% quinolines, 42.0% aminopropyl-2,4-TDA and 16.0% dicyclics.

Purification of Crude Aminopropylated-2,4-TDA

The crude aminopropylated-2,4-TDA was purified by reduced pressure fractional distillation using a 48 inch packed column and refluxed splitter. The distillation conditions were 20 mm Hg and 2:1 reflux ratio. The heart cut was taken over a temperature range of 179–187° C. 602 g of clear, yellow product were obtained, which comprised 0.6% 2,4-TDA, 15.5% quinolines, 71.4% aminopropyl-2,4-TDA and 11.4% dicyclics. The viscosity was 1485 cps @25° C.

Use of Purified Aminopropylated-2,4-TDA as Epoxy Curative

The aminopropylated-2,4-TDA was mixed with Epon 828 epoxy resin and evaluated for gel time and thin film set time. Standard methods ERF 13-70, ERF 2-82 and ASTM D 2471-94 were used to measure gel time and standard method ASTM D 5895-96 was used to measure thin film set time. Both the Epon 828 epoxy resin and the aminopropylated-2,4-TDA were placed in a incubator overnight at 25° C. 23.88 g of aminopropylated-2,4-TDA were added to 126.1 g of Epon 828 and mixed thoroughly for 1 minute prior to measuring the gel time and thin film set time. The resulting gel time and thin film set time were 116.2 minutes and 5.0 hours, respectively.

EXAMPLE 12

Hydrogenation of Cyanoethylated 2,6-Toluenediamine

The crude cyanoethylated 2,6-toluenediamine obtained in Examples 8 and 9 were combined, placed in an autoclave and treated with 500 ml of 28% ammonium hydroxide. 50 g of Raney cobalt catalyst were then added. The autoclave was sealed, purged 2 times with nitrogen and 2 times with hydrogen, and then pressurized to 900 PSI (6.21 MPa) with hydrogen. The temperature was raised to 125° C. under constant 900 PSI (6.21 MPa) hydrogen pressure. The temperature was held at 125° C. until the hydrogen consumption ceased, which usually takes about 30 minutes. The autoclave was cooled to room temperature, hydrogen vented and purged with nitrogen. The crude aminopropylated 2,6-toluenediamine was then filtered to remove the catalyst. The resultant product mixture as analyzed by GC contained 16.1% propylamine, 13.5% 2,6-TDA, 11.4% quinolines, 30.3% aminopropyl-2,6-TDA and 26.0% dicyclics.

Purification of Crude Aminopropylated-2,6-TDA

The crude aminopropylated-2,6-TDA was purified by reduced pressure fractional distillation using a 48 inch packed column and refluxed splitter. The distillation conditions were 20 mm Hg and 2:1 reflux ratio. The heart cut was taken over a temperature range of 172–178° C. 336 g of clear, yellow product was obtained, comprising 3.6% 2,6-TDA, 17.4% quinolines, 70.4% Aminopropyl-2,6-TDA and 7.2% dicyclics. The viscosity was 873 cps @ 25° C.

Use of Purified Aminopropylated-2,6-TDA as Epoxy Curative

The aminopropylated-2,6-TDA was mixed with Epon 828 epoxy resin and evaluated for gel time and thin film set time. Standard methods ERF 13-70, ERF 2-82 and ASTM D 2471-94 were used to measure gel time and standard method ASTM D 5895-96 was used to measure thin film set time. Both the Epon 828 epoxy resin and the aminopropylated-2,6-TDA were placed in a incubator overnight at 25° C. 23.88 g of aminopropylated-2,6-TDA were added to 126.1 g of Epon 828 and mixed thoroughly for 1 minute prior to measuring the gel time and thin film set time. The resulting gel time and thin film set time were 163.9 minutes and 10.5 hours, respectively.

EXAMPLE 13

Cyanoethylation of 2,4-Toluenediamine using 1-Propanol as Solvent

A 500 ml 4-necked round bottom flask was equipped with a magnetic stir bar and stirrer, thermometer, condenser, nitrogen purge and dropping funnel. The vessel was charged with 104.8 parts of 2,4-toluenediamine, 100 parts of 1-propanol and 0.3 parts of Nafion catalyst. The mixture was heated to 80–86° C. and 95 parts of acrylonitrile were added drop-wise over a 30-minute period. The mixture was refluxed for 46 hours, cooled to room temperature and collected. The organic phase of the reaction mixture contained 10.3% acrylonitrile, 25.6% 2,4-toluenediamine, 50.9% mono-cyanoethylated 2,4-toluenediamine and 7.2% di-cyanoethylated 2,4-toluenediamine according to GC analysis.

This invention provides the epoxy market with aromatic amine curatives that have the reactivity and liquid viscosity of aliphatic amine curatives, while possessing the performance properties of aromatic amine curatives, particularly chemical resistance and Tg. Conventional aromatic amine curatives must be dissolved in solvents and accelerated with catalysts, such as salicylic acid or phenol, to obtain the appropriate reactivity. Aliphatic amines, on the other hand, do not provide adequate chemical resistance.

While the invention has been described in detail and with reference to specific examples thereof, it will be apparent to one skilled in the art that various changes and modifications can be made therein without departing from the spirit and scope thereof.

We claim:

1. An N-aminopropylated toluenediamine.

2. The N-aminopropylated toluenediamine of claim 1, represented by the following formula:

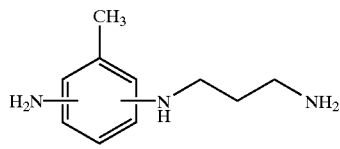

where the nitrogen atoms are ortho or meta to each other on the aromatic ring.

3. The N-aminopropylated toluenediamine of claim 1, having the designation N-(2-amino-6-methylphenyl)-1 3-propanediamine.

4. The N-aminopropylated toluenediamine of claim 1, having the designation N-(2-amino-3-methylphenyl)-1,3-propanediamine.

5. The N-aminopropylated toluenediamine of claim 1, having the designation N-(2-amino-5-methylphenyl)-1,3-propanediamine.

6. The N-aminopropylated toluenediamine of claim 1, having the designation N-(2-amino-4-methylphenyl)-1,3-propanediamine.

7. The N-aminopropylated toluenediamine of claim 1, having the designation N-(5-amino-6-methylphenyl)-1,3-propanediamine.

8. The N-aminopropylated toluenediamine of claim 1, having the designation N-(3-amino-6-methylphenyl)-1,3-propanediamine.

9. The N-aminopropylated toluenediamine of claim 1, having the designation N-(3-amino-4-methylphenyl)-1,3-propanediamine.

10. A process for preparing the N-aminopropylated toluenediamine of claim 1, said process comprising:

cyanoethylating a toluenediamine with acrylonitrile to provide a cyanoethylated toluenediamine; and hydrogenating said cyanoethylated toluenediamine to provide said N-amino-propylated toluenediamine.

11. The process of claim 10, wherein said cyanoethylating is conducted in a protic solvent containing an acid catalyst.

12. The process of claim 11, wherein said protic solvent is at least one member selected from the group consisting of water, methanol, ethanol, isopropanol and n-propanol.

13. The process of claim 11, wherein said acid catalyst is at least one member selected from the group consisting of hydrochloric acid, sulfuric acid, phosphoric acid, acetic acid, propionic acid, para-toluenesulfonic acid, triflic acid and Nafion catalyst.

14. The process of claim 11, wherein said acid catalyst is hydrochloric acid or Nafion catalyst.

15. The process of claim 11, wherein a molar ratio of toluenediamine to acrylonitrile is from 0.95:1.0 to about 1.0:2.0.

16. The process of claim 11, wherein said cyanoethylating is conducted within a temperature range from about 50° C. to about 150° C. and within a pressure range from about atmospheric pressure up to about 900 psi (6.21 MPa).

17. The process of claim 11, wherein said hydrogenating comprises contacting said cyanoethylated toluenediamine with hydrogen in the presence of a hydrogenation catalyst at a hydrogen pressure from about atmospheric pressure to about 2000 psi (13.79 MPa) and at a hydrogenation temperature from about 50° C. to about 200° C.

18. The process of claim 17, wherein said hydrogenation temperature is from about 100° C. to about 125° C.

19. The process of claim 17, wherein said hydrogen pressure is about 50 to 900 psi (0.345 to 6.21 MPa).

20. The process of claim 17, wherein said hydrogenation catalyst is Raney nickel or Raney cobalt.

21. The process of claim 17, wherein said hydrogenation catalyst is loaded in a catalyst-loading amount of 0.01 to 10.0% by weight of said N-aminopropylated toluenediamine.

22. In a method of curing an epoxy resin with a curing composition containing an amine, the improvement wherein the amine is the N-aminopropylated toluenediamine of claim 1.

23. The method of claim 22, wherein said N-aminopropylated toluenediamine represented by the following formula:

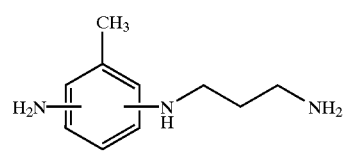

where the nitrogen atoms are ortho or meta to each other on the aromatic ring.

24. The method of claim 22, wherein said N-aminopropylated toluenediamine is N-(2-amino-6-methylphenyl)-1,3-propanediamine.

25. The method of claim 22, wherein said N-aminopropylated toluenediamine is N-(2-amino-3-methylphenyl)-1,3-propanediamine.

26. The method of claim 22, wherein said N-aminopropylated toluenediamine is N-(2-amino-5-methylphenyl)-1,3-propanediamine.

27. The method of claim 22, wherein said N-aminopropylated toluenediamine is N-(2-amino-4-methylphenyl)-1,3-propanediamine.

28. The method of claim 22, wherein said N-aminopropylated toluenediamine is N-(5-amino-6-methylphenyl)-1,3-propanediamine.

29. The method of claim 22, wherein said N-aminopropylated toluenediamine is N-(3-amino-6-methylphenyl)-1,3-propanediamine.

30. The method of claim 22, wherein said N-aminopropylated toluenediamine is N-(3-amino-4-methylphenyl)-1,3-propanediamine.

31. The method of claim 22, wherein said N-aminopropylated toluenediamine is at least one member selected from the group consisting of N-(5-amino-6-methylphenyl)-1,3-propanediamine, N-(3-amino-6-methylphenyl)-1,3-propane-diamine and N-(3-amino-4-methylphenyl)-1,3-propanediamine, and said curing composition further comprises at least one molecule represented by the following formulas:

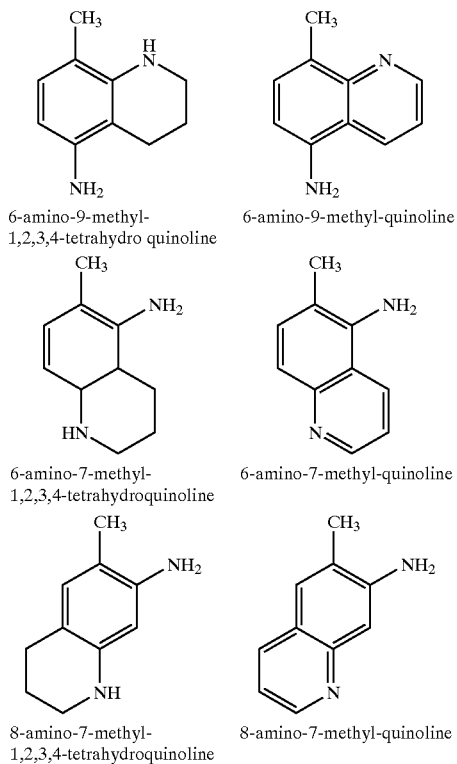

6-amino-9-methyl-1,2,3,4-tetrahydro quinoline 6-amino-9-methyl-quinoline 6-amino-7-methyl-1,2,3,4-tetrahydroquinoline 6-amino-7-methyl-quinoline 8-amino-7-methyl-1,2,3,4-tetrahydroquinoline 8-amino-7-methyl-quinoline -continued

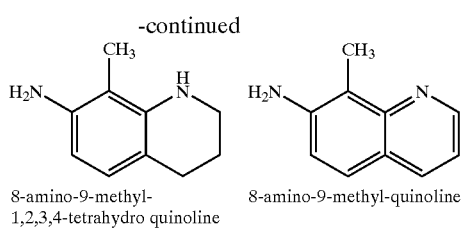

8-amino-9-methyl-1,2,3,4-tetrahydro quinoline 8-amino-9-methyl-quinoline

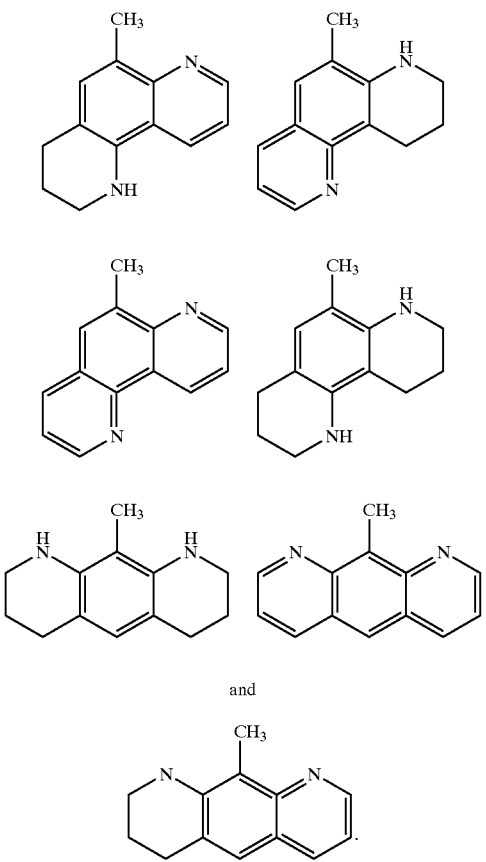

and

* * * * *